United States Patent [19]

Ksander et al.

[11] Patent Number: 4,772,285

[45] Date of Patent: Sep. 20, 1988

[54] COLLAGEN COATED SOFT TISSUE PROSTHESES

[75] Inventors: George Ksander, Menlo Park; Leonard Gray, Los Angeles, both of Calif.

[73] Assignee: The Board of Trustees of the Leland Stanford Junior University, Stanford, Calif.

[21] Appl. No.: 925,464

[22] Filed: Oct. 30, 1986

Related U.S. Application Data

[63] Continuation of Ser. No. 608,397, May 9, 1984, abandoned.

[51] Int. Cl.$^4$ ............................................... A61F 2/12
[52] U.S. Cl. .................................... 623/8; 128/DIG. 8
[58] Field of Search ............ 623/8; 128/335.5, DIG. 8

[56] References Cited

U.S. PATENT DOCUMENTS

| | | | |
|---|---|---|---|
| 3,276,448 | 10/1966 | Kronenthal | 3/1 |
| 3,955,012 | 4/1976 | Okamura | 128/DIG. 8 |
| 3,986,213 | 10/1976 | Lynch | 3/36 |
| 4,233,360 | 11/1980 | Luck et al. | 514/801 X |
| 4,428,082 | 1/1984 | Naficy | 623/8 |

OTHER PUBLICATIONS

McGrath et al., (1984) Plastic Reconstr. Surg. 74:550-560.
Vistnes et al., in Biomaterials in Reconsutructive Surgery, pp. 516-528 (L. R. Rubin ed. 1983).
Blais in ibid, pp. 544-551.
Rudolph in ibid, pp. 576-587.

*Primary Examiner*—Richard J. Apley
*Assistant Examiner*—Alan W. Cannon
*Attorney, Agent, or Firm*—Ciotti & Murashige, Irell & Manella

[57] ABSTRACT

An improved soft tissue implant which resists capsule formation and contracture is described. The implant is coated with a non-immunogenic collagen preparation optionally stabilized by crosslinking.

14 Claims, No Drawings ured to be compatible with soft
COLLAGEN COATED SOFT TISSUE PROSTHESES This application is a continuation of application Ser. No. 608,397, filed May 9, 1984, now abandoned.

FIELD OF THE INVENTION

The invention relates to the field of implant prostheses used to reconstruct soft tissue. More specifically, it concerns soft tissue prostheses coated with collagen effective in preventing rapid capsule formation.

BACKGROUND ART

A commonly encountered defense mechanism by which an organism protects itself against a foreign body is the formation of a capsule enclosing and isolating the foreign material. Capsule formation, while desirable with respect to the organism as a general proposition, is disadvantageous when a prosthesis is deliberately implanted and the desired result is the integration of the implant into the surrounding tissue. Perhaps the best known instance of such implants is in breast enhancement and in tissue reconstruction employing silicone rubber implants.

The scenario which gives rise to the problem this invention is designed to solve is, briefly, as follows: The implanted silicone is rapidly encapsulated by a fiber structure, composed primarily of collagen and glycosaminoglycans, and containing fibroblasts and histiocytes. The capsule then contracts, resulting in hardening and spherical deformation of the implant itself, as well as of the surrounding tissues. The implant then becomes painful, aesthetically unacceptable, and, if untreated, can result in erosion of the overlying tissues and extrusion of the implant.

The success of mammoplasty and post-mastectomy reconstruction, as well as of other procedures involving implants of soft tissue prostheses, would be greatly enhanced by use of a prosthesis which does not elicit encapsulation, or which is resistant to capsule contraction. The present invention provides soft tissue implants which resist encapsulation and subsequent contracture.

DISCLOSURE OF THE INVENTION

The invention takes advantage of the observation that injectable soluble atelopeptide collagen, for example, in the commercially available form known as ZYDERM ® collagen implant (ZCI), does not provoke capsule formation. In the method of the invention, the soft tissue implant is first coated with a reconstituted preparation of soluble collagen and then is used according to conventional procedures for reconstructive or other surgery. The problems associated with encapsulation and capsule contraction do not occur.

Thus, in one aspect, the invention relates to a soft tissue prosthesis which is resistant to encapsulation, which prosthesis comprises an alloplastic body coated with a layer of reconstituted atelopeptide collagen.

In other aspects, the invention relates to methods of preparing soft tissue implants of this description, and of using them in surgical procedures.

MODES OF CARRYING OUT THE INVENTION

A. Definitions

As used herein, "capsule" refers to a surrounding tissue growth encasing an implanted foreign soft prosthesis which tissue is, most commonly, a fibrous structure composed primarily of collagen and glycosaminoglycans, containing fibroblasts and histiocytes. It is essentially connective tissue and is capable, under suitable conditions, of contraction or shrinkage.

"Soft tissue prosthesis" or "soft tissue implant" refer to macroscopic bodies (as opposed to injectable preparations) which are designed to be compatible with soft tissue such as, for example, breast tissue, muscle, or other non-bone tissues. Typical soft tissue prostheses are constructed of silicone gel or Dacron or polyurethane, or combinations thereof, but most preferably of silicone. They are deformable (alloplastic) structures which mimic the resilience of the soft tissue into which they are implanted.

"Soft tissue construction" refers to procedures whereby non-skeletal tissue is either replaced, reformed, or enhanced by virtue of the insertion of a soft tissue implant. Typical examples of such procedures include reconstructive surgery such as that intended to repair damaged limbs or facial features which have been deformed or destroyed by trauma, plastic surgery which is intended for cosmetic purposes, reconstructions to correct birth defects, and remodeling of body features such as that increasing breast size. The foregoing list is not meant to be exhaustive, but to exemplify the kinds of reconstruction which are suitable for application of the implants of the invention.

"Collagen coating," as used herein, specifically refers to a covering of collagen spread over the entire surface of a soft tissue implant prior to its use in soft tissue construction surgery. It does not refer to the collagen-rich capsule which is formed by the host organism to the inserted mass.

"Collagen" suitable for this application includes fibrillar or insoluble collagen, with the telopeptides removed. Reconstituted collagen is preferred, because of convenience and availability; however, other forms, which have not been processed, as has reconstituted collagen, by solubilization followed by reprecipitation can also be used. Indeed, collagen in solution could be applied directly to the prosthesis and the solvent evaporated, or sheets of intact collagen materials wrapped to surround the implant.

B. The Improved Prosthesis

The improved prosthesis of the invention comprises a typical soft tissue implant, such as, for example, a silicone gel bag, which is completely coated with a collagen layer so as to preclude contact of the foreign material of the implant with the surrounding tissue. The collagen coating is composed of fibers or an amorphous preparation of mostly Type I collagen from which the telopeptides have been removed by enzyme treatment. The fibrillar or amorphous collagen resulting from such treatment is in triple helix form, lacking immunogenic peptides found in natural collagen. Suitable collagen preparations can be obtained from skin, bone, or other connective tissue, but most conveniently from skin. Such preparations are, indeed, commercially available under the trademark ZYDERM ® collagen implant (ZCI).

C. Methods of Constructing the Improved Prosthesis

There are a variety of methods of manufacture available to provide a collagen coating to the prosthetic devices useful in the invention. The resulting coating is preferably uniform, and must be integral so that contact between the ordinary prosthesis and the surrounding tissue is precluded. The coating could be provided by spraying the prosthesis with a suspension of, for example, ZCI, and permitting the surface to dry, by dipping the prosthesis into such a suspension, or by casting a suspension of ZCI over the entire surface. These procedures, while operative, are less desirable than an alternative approach which not only provides the desired coating, but also provides a space between the coating and the original prosthesis. This can be accomplished by using a mold which has been coated with the collagen suspension, which mold is slightly larger than the prosthesis to be coated.

For example, in one embodiment of this process, a model prosthesis is enhanced in size by coating of, for example, paraffin. The thus enlarged prosthesis is then used as a model for a two-piece mold of casting resin which can be split away into the two halves after solidifying around the enlarged prosthesis.

The mold is then washed and each half supplied with a sufficient quantity of collagen suspension so that when a new prosthesis is inserted and the mold resealed around it, the collagen spreads over the entire surface to form a uniform coating. After sealing, the assembly is incubated to solidify partially the collagen layer. After removing the mold, any uncoated areas are covered with additional ZCI; preferably, however, sufficient ZCI is added initially that such areas are not present.

A still more preferred mode of prepration employs an additional step which results in crosslinking of the collagen coat. The presence of crosslinks aids in preserving the integrity of the coating and rendering it resistant to indigenous tissue enzymes which would otherwise weaken it. In a typical preparation, the collagen is applied as suggested above, preferably without the use of a mold, by dipping or coating, and the coated implant is, after suitable incubation and washing, for example, with acetone, placed in a bath of aqueous aldehyde, such as formaldehyde or glutaraldehyde, to effect the desired crosslinks. The application of crosslinking material can, of course, also be done by painting, coating or any other standard means. After the crosslinking agent is applied, the implant is again rinsed and dried.

More than one coat of either untreated or crosslinked (preferably crosslinked) material can be applied. It is highly desirable to inspect the resulting coated prosthesis carefully to insure that no gaps or breaks are present in the coating.

D. Method of Implantation

The methods used for implanting the collagenencased implant are analogous to those used for ordinary soft tissue implants, and, of course, depend on the nature of the condition to be modified or corrected. The surgery can be performed under either local or systemic anesthesia and, generally, involves an incision, spacing to accomodate the implant, insertion, and suture.

E. Examples

The following examples are intended to illustrate the invention but not limit it. The effectiveness of the collagen encasement was established using an animal model and evaluating the status of each implant, whether or not coated with collagen.

E.1 Molded and Coated Silicone Bag-Gel Prosthesis

E.1.a Preparation of the Implant

Silicone bag-gel miniprostheses, obtained from Medical Engineering Corporation, Racine, Wis., having a diameter of 2 cm and a volume of approxiately 2 ml were used. These were intended as breast implants and consist of a soft silicone rubber shell containing a viscous silicone gel filling.

To increase the dimensions of the implant, and thereby provide a space between the implant and the eventual mold, the prosthesis was repeatedly dipped into melted paraffin, cooled to 0° C., and trimmed with a sharp blade. The coated prosthesis was placed dome side down in a cup of resin consisting of Douglass and Sturgess No. 3 styrene monomer clear casting resin with 1% polyester as catalyst/hardener so that one half of the implant was exposed to air. After 6 hours for hardening, the exposed surface was painted with hot paraffin, and covered with resin and the complete mold allowed to harden overnight. It was then split along the paraffin seam, the prosthesis and excess paraffin removed, and the mold was washed and dried. Approximately 1 ml of ZYDERM ® collagen implant (Collagen Corporation, Palo Alto, Calif.) was placed in each half of the mold, and a new miniprosthesis, as removed from the manufacturer's packing, was inserted. The two halves were pressed together, sealed with tape, and the assembly was incubated at 37° C. for 1 hour. The prosthesis was removed and inspected, and any uncoated areas were covered with additional ZCI applied manually. The implant was re-incubated for another hour, and the coated implant then washed in 6 alternating baths of acetone and water at room temperature, dried at 37° C. for 3 days, and stored in 95% ethanol. Just prior to use, the collagen coating was rehydrated by immersing the implant in sterile normal saline. The coating was ideally a continuous non-adherent skin loosely enclosing the implant.

E.1.b Insertion of the Implants

Bilateral dorsal pockets in the subcutaneum of 12 female Sprague-Dawley rats (200–220 g) were created by blunt disection through paired paravertebral incisions under halothane anesthesia. Each animal received one coated implant and one control implant on opposite sides, alternating sides on successive animals. The control implants were similar miniprostheses without collagen coating which had been washed with soap and water, rinsed, bathed in isopropyl alcohol for 10 to 20 minutes and air dried.

E.1.c Evaluation of Results

Animals were caged in 3 groups of 4 animals, and at 60 and 120 days, one-half of the animals in each cage were sacrificed with chloroform. The dimensions of the implant mounds in the longitudinal and lateral directions were measured with a caliper, and then the implants, adherent loose connective tissue and overlying skin were disected free from the deep fascia. The tissue and the enclosed prostheses were placed in 10% Formalin ® solution for fixation with shape intact, and after 48 hours the tissue block was bisected to ensure adquate perfusion of the inner capsule. Cross-sections of the center of each block containing skin and complete capsule were imbedded in paraffin, sectioned at 6 μm, and stained with H&E or Masson's trichrome and assayed by reticular techniques. The presence or absence of a collagen coating was easily ascertainable. Certain of the results are shown below in Table 1.

TABLE 1

|  | 60 Days | | 120 Days | |
| --- | --- | --- | --- | --- |
|  | Coated X | Control X | Coated X | Control X |
| Height (cm) | nd | nd | .8 | .8 |
| Length (cm) | 2.6 | 2.4 | 2.5 | 2.5 |
| Width (cm) | 2.5 | 2.5 | 2.4 | 2.5 |
| Length/width | 1.0 | 1.0 | 1.0 | 1.0 |
| Thickness (mm) | .04 | .10 | .07 | .08 |

(nd = not done)

As seen from these results, the overall length and width of the implants was the same for both coated and control samples. However, after 60 days, the average thickness of the capsule around control samples was more than twice as great (0.1 mm) than that of the coated sample (0.04 mm). After 120 days, this difference appeared to be less; however, these averages overlook the presence in the coated implant specimens of many regions in which no capsule was seen. Indeed, the presence of capsule at 120 days was clearly associated with regions of the implant in which the coating had been imperfectly formed.

Histological examinations showed that at both 60 and 120 days all control implants were surrounded by the normal capsule which has a slightly vascular fibrous structure laminated parallel to the implant surface containing elongated fibroblasts as well as round cells. The capsule is not adherent to the implant and only tenuously continuous with the surrounding connective tissue. In H&E stained sections, the applied collagen coat appeared as a pale homogenous eosinophilic region of variable extent, continuity, and density; in trichrome stained sections, the coating was intense blue. Fine fibrils could be distinguished within the collagen coating and these were frequently oriented in linear rays parallel to the implant surface. Trichrome stain demonstrated the occasional presence of a thin acellular acidophilic lining at the prosthesis coating interface.

Accordingly, it was possible to obtain visual data as to the presence or absence of the coating at a particular location on an implant. The detection of collagen coating was made easier by virtue of its demonstrable birefringence in polarized light. Growth of any surrounding capsule was clearly associated with the absence of the coating, and thus due to imperfections in the preparation procedure, rather than to lack of efficaciousness of the coating itself.

Variable amounts of collagen coating were seen in all 60-day specimens from the coated group, and in 4 of the six 120-day specimens. In this group, 2 out of the 6 did not have remaining coating at all. At 60 days, 5 of 6 coated implants were rated as either having no capsule or partial, very slight capsule in limited regions at the interface between the coating and the silicone envelope. At 120 days, 3 of 6 coated implants had normal capsule, while each of the other 3 had varying amounts of capsule in various regions of the surface. Importantly, in all cases of coated implants which had locally variable amounts of capsule, regions in which there was coating present had very little if no capsule, while regions in which the coating was not evident had more extensive capsule formation.

It was noted that cells, predominantly fibroblasts and monocytes without inflammation, were capable of infiltration of the collagen coat; however, this infiltration was usually via discontinuities in the collagen coat.

Qualitative histological evaluation showed that at 60 days there was less capsule around coated implants than around controls. While this difference appeared to decrease at 120 days, there were still present in the coated implant specimens many more regions in which no capsule was seen than in the control samples. Histological examination also showed that the collagen coat appeared to disappear in several cases between 60 and 120 days, and this accounted for capsule formation.

While not pertinent to the effectiveness of the invention, it was also concluded that the ZCI coating is modified in this process. Evidence for this comes from the birefringence exhibited by the coated implants; this property is not characteristic of the collagen preparation used for coating; thus, an ordered structure not originally present is introduced as a result of the coating process.

E.2 Crosslinked Collagen Coating Silicone Implants

E.2.a Preparation of Implant

The incidence of experimental capsule contracture depends on the nature of the prosthesis, and prostheses furnished by various manufacturers differ in this respect. (See: Ksander, G. A., et al, *Trans of VIII Intl Cong of Plastic & Reconstructive Surgery* (1983) p. 66.) The implants used in the work described in this paragraph E.2 were silicone-gel mini prostheses of 2 cm length and 2 ml volume, obtained from Heyer-Shulte Corp., Goleta, Calif., which show a high level of capsule formation and contracture.

Twenty-one implants were coated, and 12 were used as controls.

Thirteen implants were coated using formalin crosslinking as follows:

The implant was placed on a spot of collagen suspension (ZCI) spread on parafilm, and additional suspension was then extruded onto the remaining surface of the prostheses directly from a syringe. Following incubation at 37° C. for 2 hours, and 5 minutes exposure in an acetone bath, the implant and first layer were rinsed 3 times in distilled water, then washed in 3 changes of 50 ml of distilled water. Any defects in the coating were patched using additional suspension and the coated prostheses reincubated and washed. The coated prostheses were placed in a bath of 2.5% aqueous Formalin ® solution (2.5 ml of 37% formaldehyde diluted to 100 ml with distilled water) for 20 seconds and then rerinsed and washed as above, prior to air drying at 37° C. overnight. After inspection to eliminate any prostheses damaged by the drying process, the whole process was repeated to produce a second layer. The completed coated implant was stored dry and rehydrated in normal saline prior to implantation.

Eight implants were coated and subjected to glutaraldehyde crosslinking, using a poocess similar to that of the previous paragraph, except that instead of formaldehyde, the coatings were exposed to 0.01% aqueous glutaraldehyde overnight at room temperature, and washing consisted of 4–5 changes of distilled water, 500 ml/change, overnight.

E.2.b Insertion of Implants

Experimental coated prostheses were implanted subcutaneously as described in paragraph E.1.b, except that separate animals were used as controls using uncoated implants.

E.2.c Evaluation

At approximately 15-day intervals, the animals were anesthetized, and the implant mounds were shaved. Each mound was then subjectively rated as being "contracted", i.e., visibly distorted into an elongated ovoid shape, or "normal", i.e., symmetrical in shape. The length of each mound in the cephalo-caudal direction and its width in the dorso-ventral direction were measured with a caliper. The results after 13 days and 28 days were consistent with those shown in Table 2 taken at 46 days after surgery.

TABLE 2

|  | Control N = 12 | Formaldehyde N = 13 | Glutaraldehyde N = 8 |
| --- | --- | --- | --- |
| % contracted | 91.7% | 0% | 0% |
| mound length (cm) | 2.2 | 2.8 | 2.7 |
| mound width (cm) | 2.8 | 2.7 | 2.7 |
| length/width | .8 | 1.0 | 1.0 |

The data demonstrates that none of the collagen coated implants showed contracture, even though contracture occurred in 11 of the 12 control animals. Where contracture occurs, shrinkage takes place in the cepalocaudal direction, with little change in the dorso-ventral dimension.

We claim:

1. An improved breast implant which is resistant to encapsulation comprising an alloplastic breast prosthesis encased in an integral coating consisting essentially of atelopeptide collagen, wherein said integral coating directly adheres the solid surface of said alloplastic breast prosthesis.

2. The implant of claim 1 wherein the collagen is reconstituted.

3. The implant of claim 1 wherein the alloplastic prosthesis is a silicone gel prosthesis.

4. The implant of claim 1 wherein the collagen coating is crosslinked.

5. The implant of claim 4 wherein the crosslinking is effected by fomaldehyde or glutaraldehyde.

6. A method of making a breast implant resistant to encapsulation comprising coating an alloplastic breast prosthesis with reconstituted atelopeptide collagen, whereby said reconstituted atelopeptide collagen forms an integral coating that directly adheres to the solid surface of said alloplastic breast prosthesis.

7. The method of claim 6 wherein the collagen is reconstituted.

8. The method of claim 6 wherein the alloplastic prosthesis is a silicone prosthesis.

9. The method of claim 6 which includes the step of crosslinking the collagen coating.

10. The method of claim 9 wherein the crosslinking is effected by glutaraldehyde or formaldehyde.

11. The method of claim 6 wherein the collagen coating is applied in 2 sequential layers.

12. A method of supplementing mammary tissue which comprises surgical implantation of the improved prosthesis of claim 1.

13. A method of supplementing mammary tissue which comprises surgical implantation of the improved prosthesis of claim 1.

14. The implant of claim 1 wherein the alloplastic prosthesis is a silicone prosthesis.

* * * * *

UNITED STATES PATENT AND TRADEMARK OFFICE
CERTIFICATE OF CORRECTION

PATENT NO. : 4,772,285
DATED : 20 September 1988
INVENTOR(S) : George Ksander and Leonard Gray It is certified that error appears in the above-identified patent and that said Letters Patent is hereby corrected as shown below:

In Claim 1, column 8, line 1, insert --to-- between "adheres" and "the".

Signed and Sealed this

Fourteenth Day of February, 1989

*Attest:*

DONALD J. QUIGG

*Attesting Officer*    *Commissioner of Patents and Trademarks*